United States Patent
Brown et al.

(10) Patent No.: US 10,682,611 B2
(45) Date of Patent: Jun. 16, 2020

(54) SYSTEM AND METHOD FOR CONTROLLING OUTLET FLOW OF A DEVICE FOR SEPARATING CELLULAR SUSPENSIONS

(71) Applicant: Fenwal, Inc., Lake Zurich, IL (US)

(72) Inventors: Richard I. Brown, Northbrook, IL (US); Benjamin E. Kusters, Pleasant Prairie, WI (US); Kyungyoon Min, Kildeer, IL (US)

(73) Assignee: Fenwal, Inc., Lake Zurich, IL (US)

( * ) Notice: Subject to any disclaimer, the term of this patent is extended or adjusted under 35 U.S.C. 154(b) by 237 days.

(21) Appl. No.: 15/894,307

(22) Filed: Feb. 12, 2018

(65) Prior Publication Data

US 2018/0236405 A1    Aug. 23, 2018

Related U.S. Application Data

(60) Provisional application No. 62/461,910, filed on Feb. 22, 2017.

(51) Int. Cl.
*B01D 61/38* (2006.01)
*B01D 15/18* (2006.01)
(Continued)

(52) U.S. Cl.
CPC .............. *B01D 61/38* (2013.01); *A61M 1/265* (2014.02); *A61M 1/3403* (2014.02);
(Continued)

(58) Field of Classification Search
None
See application file for complete search history.

(56) References Cited

U.S. PATENT DOCUMENTS 5,423,738 A * 6/1995 Robinson ............ A61M 1/0052
604/6.01
6,080,322 A * 6/2000 Deniega ................ A61M 1/30
210/739

(Continued)

FOREIGN PATENT DOCUMENTS

WO    WO97/05938 A1    2/1997
WO    WO2011/128465 A1    10/2011

OTHER PUBLICATIONS

Extended European Search Report, counterpart EP Appl No. 18156690, dated Jun. 22, 2018.

*Primary Examiner* — Krishnan S Menon
(74) *Attorney, Agent, or Firm* — Cook Alex Ltd.

(57) ABSTRACT

A system for separating a suspension of biological cells is disclosed comprising a single-use fluid circuit and a durable hardware component. The fluid circuit comprises a separator having a housing that includes an inlet for introducing the suspension of biological cells into the gap, a first outlet in communication with the gap for flowing a first type of cells from the separator, and a second outlet in communication with the second side of the filter membrane for flowing a second type of cells from the separator. The hardware component comprises a pump for flowing the suspension of biological cells to the inlet of the separator and at least one flow control device associated with the first outlet and the second outlet of the separator for selectively opening and closing the outlets so as to permit one of the first type of cells and the second type of cells to flow out of the separator in accordance with a predetermined duty cycle equal to the ratio of a target flow rate of first type of cells through the first outlet to the predetermined inlet flow rate.

16 Claims, 7 Drawing Sheets

(51) Int. Cl.
*B01D 15/12* (2006.01)
*B01D 63/16* (2006.01)
*B01D 61/22* (2006.01)
*A61M 1/34* (2006.01)
*A61M 1/26* (2006.01)
*B01D 63/06* (2006.01)

(52) U.S. Cl.
CPC ......... *A61M 1/3496* (2013.01); *B01D 15/125* (2013.01); *B01D 15/18* (2013.01); *B01D 61/22* (2013.01); *B01D 63/06* (2013.01); *B01D 63/16* (2013.01); *B01D 2313/08* (2013.01); *B01D 2313/18* (2013.01); *B01D 2313/48* (2013.01); *B01D 2315/02* (2013.01); *B01D 2315/10* (2013.01); *B01D 2315/18* (2013.01)

(56) References Cited

U.S. PATENT DOCUMENTS

| | | | |
|---|---|---|---|
| 2010/0192686 A1* | 8/2010 | Kamen | A61M 1/16 73/290 R |
| 2013/0341274 A1* | 12/2013 | Kusters | A61M 1/34 210/646 |
| 2013/0345674 A1 | 12/2013 | Kusters et al. | |

* cited by examiner

SYSTEM AND METHOD FOR CONTROLLING OUTLET FLOW OF A DEVICE FOR SEPARATING CELLULAR SUSPENSIONS

FIELD OF THE INVENTION

The present disclosure is directed to methods for controlling flow through a device for the separation of biological cells in a suspension using a pulse width modulation technique, and to and systems employing such methods. The method controls the outlet flow rate from the separator by alternating between an open and closed first outlet line, with a second outlet line being open or closed opposite to the first outlet line. Modulation of the ratio of time that the first outlet line is open to the time that the first outlet line is closed defines a duty cycle that determines the outlet flow rates through both the first and second outlet lines. In a specific example, the separator comprises a membrane separation system and the method controls the fluid flowing out of the first outlet line (through which the retentate flows) and the second outlet line (through which the filtrate flows) using the pulse width modulation technique.

BACKGROUND

The use of devices for the separation of whole blood or into its constituent components is widespread. Such devices commonly utilize centrifuges (that separate the cellular components based on their density) or filter membranes (that separate the cellular components based upon their size).

Typically, the control of fluid into and out of a centrifugal or spinning membrane separation device has been accomplished by applying a first pump to the inlet line of the separator to supply a blood source, and a second pump applied to either a first outlet line (for the retentate, in the case of a spinning membrane separator) or a second outlet line (for the filtrate in the case of a spinning membrane separator) to control the flow of fluid through the membrane.

In the case of a spinning membrane separator, to force a fluid to flow across a membrane a gradient must be formed across the membrane. For a spinning membrane separator, a pressure gradient, commonly referred to as the transmembrane pressure (TMP), is generated to force fluid (filtrate) to flow through the membrane while particles or cells (retentate) greater than the membrane pore size are retained. See, e.g., US 2013/0345674, which is incorporated herein by reference. For example, if the inlet pump is pumping at 50 ml/min and the retentate pump in pumping at 30 ml/min, a TMP will be produced and filtrate will flow through the membrane at 20 ml/min (difference between inlet and retentate rates).

While the use of a pump on each of the inlet line and outlet line(s) of the separation system has proven to be effective for many applications, there is a desire to simplify the required hardware and to reduce the size of the system.

SUMMARY

By way of the present disclosure, a cellular separation system and method are provided in which the pump associated with one of the outlets of the separator is eliminated, and an automated clamp or stopcock is instead associated with each of a first and second outlet line for controlling flow out of the separator. Actuation of the clamps/stopcocks to alternately open and close the two outlet lines in opposition to each other permits the use of a pulse width modulation (PWM) technique to control the outlet flow from the separator. Opening and closing the two outlet lines in opposition for specific time durations permits the achievement of a specific average flow rate out of the separator.

In a first aspect, a system for separating a suspension of biological cells is provided comprising a durable hardware component and a single use fluid circuit. The fluid circuit comprises a separator having a housing with an inlet for introducing the suspension of biological cells into the separator, a first outlet in communication with the separator for flowing a first type of cells from the separator and a second outlet in communication with separator for flowing a second type of cells from the separator, and a hardware component comprising a pump for flowing the suspension of biological cells to the inlet of the separator, at least one flow control device associated with the first outlet and the second outlet of the separator for selectively opening and closing the first and second outlets so as to permit one of the first type of cells and the second type of cells to flow out of the separator.

In a specific example, the fluid circuit comprises a spinning membrane separator having a housing and a relatively-rotatable filter membrane having a first side and a second side. A gap is defined between the housing and the first side of the filter membrane, while a flow path is provided that is in fluid communication with the second side of the filter membrane. The housing includes an inlet for introducing the suspension of biological cells into the gap, a first outlet in communication with the gap for flowing the first type of cells from the separator, and a second outlet in communication with the second side of the filter membrane for flowing the second type of cells from the separator.

The hardware component comprises a pump for flowing the suspension of biological cells to the inlet of the separator. At least one flow control device is associated with the first outlet and the second outlet of the separator for selectively opening and closing the first and second outlets so as to permit one of the first and second types of cells to flow out of the separator. The flow control device(s) may comprise a clamp for each outlet line from the separator. Alternatively, the flow control device may comprise a two-way stopcock that connects to both of the two outlet lines from the separator.

The hardware component further comprises a programmable controller configured to operate the pump so as to flow the suspension of biological cells to the inlet of the separator at a predetermined inlet flow rate and to alternately open and close the flow control device in accordance with a predetermined duty cycle. More specifically, the programmable controller is configured to alternately open and close the flow control device(s) such that the duty cycle is equal to the ratio of a target flow rate of the first type of cells through the first outlet to the predetermined inlet flow rate.

In a second aspect, the programmable controller is further configured to determine the target flow rate of first type of cells as the product the inlet flow rate times the ratio of cell concentration of the suspension of biological cells to a target cell concentration of the first type of cells.

In a third aspect, the programmable controller is further configured to alternately open and close the flow control device at a predetermined frequency.

In a fourth aspect, the programmable controller is further configured to establish the predetermined frequency for the duty cycle based on the concentration of cells in the suspension of biological cells being separated.

In a fifth aspect, the predetermined frequency for the duty cycle is directly proportional to the concentration of cells in the suspension of biological cells being separated.

In a sixth aspect, a method for separating a suspension of biological cells is provided using a system as described above, comprising operating the pump so as to flow the suspension of biological cells to the inlet of the separator at a predetermined inlet flow rate, and alternately opening and closing the flow control device(s) in accordance with a predetermined duty cycle. More specifically, the method comprises alternately opening and closing the flow control device(s) such that the duty cycle is equal to the ratio of a target flow rate of a first type of cells through the first outlet to the predetermined inlet flow rate.

In a seventh aspect, the method comprises determining the target flow rate of the first type of cells as the product the inlet flow rate times the ratio of cell concentration of the suspension of biological cells to a target cell concentration of the first type of cells.

In an eighth aspect, the method comprises alternately opening and closing the flow control device at a predetermined frequency.

In a ninth aspect, the method comprises establishing the predetermined frequency for the duty cycle based on the concentration of cells in the suspension of biological cells being separated.

In a tenth aspect, the predetermined frequency for the duty cycle is directly proportional to the concentration of cells in the suspension of biological cells being separated.

DETAILED DESCRIPTION

A more detailed description of the systems and methods in accordance with the present disclosure is set forth below. It should be understood that the description below of specific devices and methods is intended to be exemplary, and not exhaustive of all possible variations or applications. Thus, the scope of the disclosure is not intended to be limiting, and should be understood to encompass variations or embodiments that would occur to persons of ordinary skill.

While the following describes the method in the context of system that utilizes a spinning membrane separator, the method is equally applicable to systems that use other types of separation devices, such as centrifuges. Terms that relate specifically to membrane filtration, such as "retentate" and "filtrate", are understood to have counterparts in centrifugal separation. Thus "retentate" should be broadly understood to refer to a first type of blood cell in the suspension, while "filtrate" should be understood to refer to a second type of blood cell in the suspension and/or a non-cellular fluid (e.g., plasma) in which the blood cells are suspended. Similarly, in the context of unspecified types of separators, reference to "a second type of cells" should be understood to include a second type of blood cell in the suspension and/or the non-cellular fluid in which the blood cells are suspended.

Figure 1:
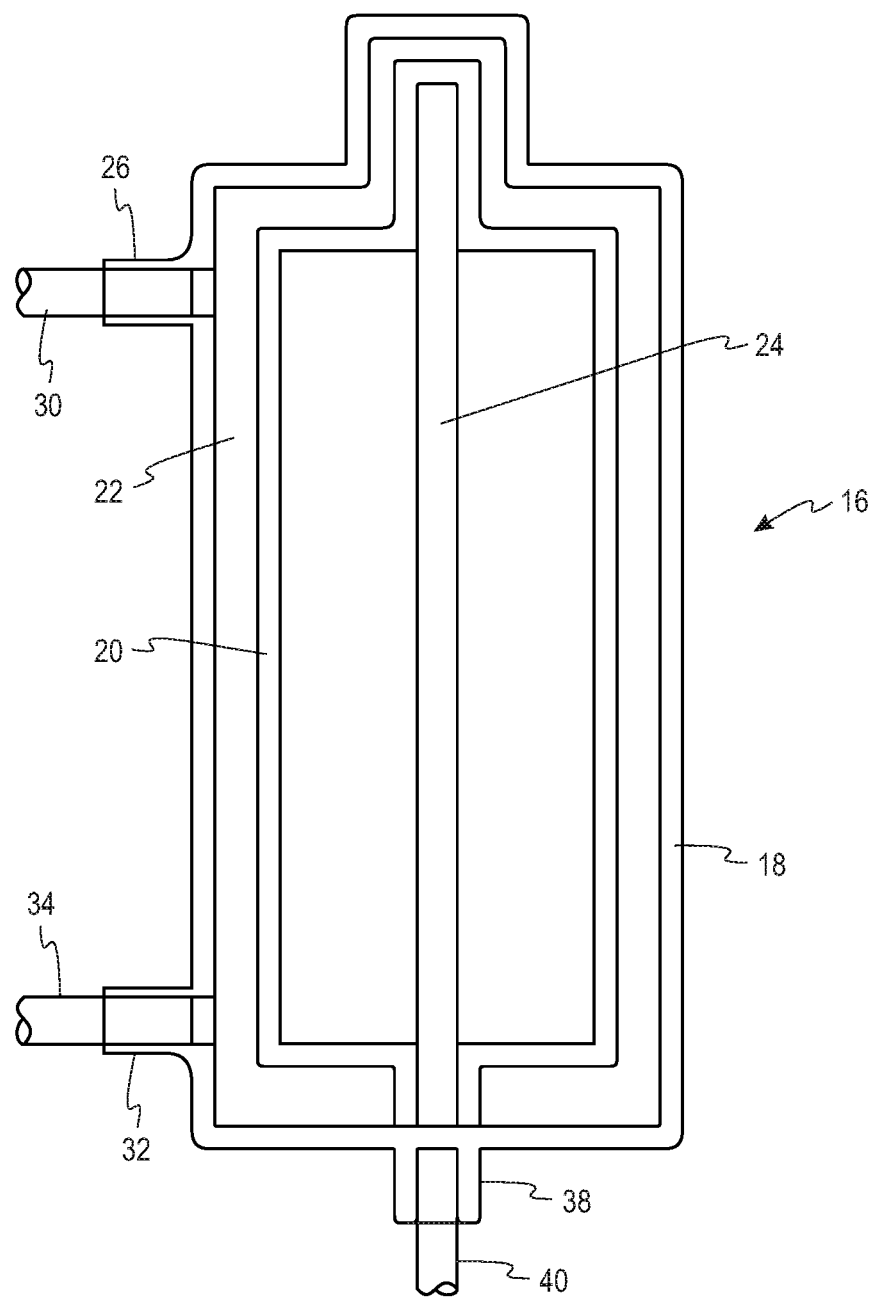
FIG. 1 is a schematic cross-sectional view of a spinning membrane separator of the type that may be advantageously used in the system and method of the present disclosure.

Turning to the FIGS. 1-3, a system 10 for separating a suspension of biological cells is provided comprising a durable hardware component 12 and a single use fluid circuit 14. The fluid circuit 14 comprises a spinning membrane separator 16 (best seen in FIG. 1) having a housing 18 and a relatively-rotable filter membrane 20 having a first side and a second side. A gap 22 is defined between the housing 18 and the first side of the filter membrane, while a flow path 24 is provided that is in fluid communication with the second side of the filter membrane 20.

The housing 18 includes an inlet 26 for introducing the suspension of biological cells into the gap 22 to which a source of the biological suspension to be separated (reservoir 28) is connected by a first tubing segment 30. While the suspension to be separated is shown as being contained in a reservoir 28, it could also be sourced directly from a donor by means of a donor access device (such as a phlebotomy needle) on the free end of the first tubing segment 30.

The housing 18 further includes a first outlet 32 in communication with the gap 22 for flowing retentate from the separator 16 through a second tubing segment 34 to a first collection container 36, and a second outlet 38 in communication with the flow path 24 on the second side of the filter membrane for flowing filtrate from the separator through a third tubing 40 segment to a second collection container 42. In one example, the suspension of biological cells may be whole blood, the retentate may be red blood cells and the filtrate may be plasma. In a second example, the suspension of biological cells may be platelet rich plasma, the retentate may be a platelet concentrate and the filtrate may be platelet free plasma.

The hardware component 12 comprises a pump 44 that cooperatively engages the first tubing segment 30 for flowing the suspension of biological cells to the inlet 26 of the separator 16. At least one flow control device is associated with each of the second and third tubing segments 34, 40, that are in fluid communication with the first outlet and the second outlets 32, 38, respectively, of the separator 16. These flow control devices selectively alternately open and close the second and third tubing segments so as to permit one of the retentate and the filtrate to flow out of the separator through the first and second outlets. With reference to the embodiment of FIGS. 2A and 2B, the flow control devices comprise clamps 46, 48 respectively associated the second and third tubing segments 34, 40. With reference to the embodiment of FIGS. 3A and 3B, the flow control device comprises a two-way stopcock 50 that is connected to both the second and third tubing segments 34, 40.

The hardware component 12 further comprises a programmable controller 52 configured to operate the pump 44 so as to flow the suspension of biological cells to the inlet 26 of the separator 16 at a predetermined inlet flow rate, and to alternately open and close the flow control device(s) 46, 48, 50 in accordance with a predetermined duty cycle. More specifically, the programmable controller 52 is configured to alternately open and close the flow control device(s) 46, 48, 50 such that the duty cycle is equal to the ratio of a target flow rate of retentate through the first outlet to the predetermined inlet flow rate. As illustrated, the hardware component also includes a pressure sensor 54 for measuring the fluid pressure at the inlet 26 of the separator 16.

As noted above, the flow of fluid out of the spinning membrane separator 16 is controlled by applying a pulse width modulation (PWM) technique. Thus, fluid flow through the spinner gap 22 and across the spinning membrane 20 is accomplished by using a single pump 44 to control the inlet rate, and PWM, rather than second pump, is used to control the outlet rate.

Figure 2A:
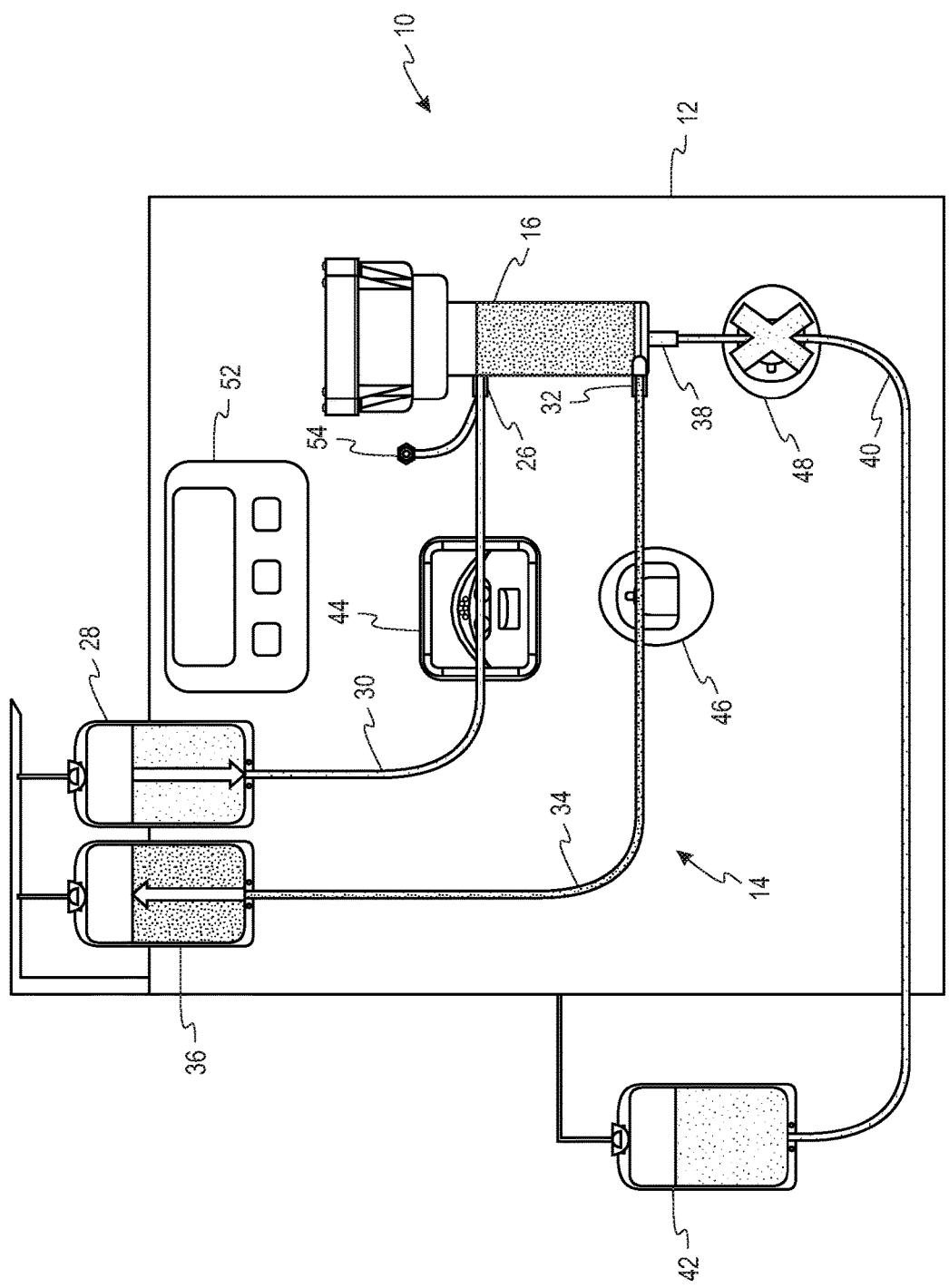
FIGS. 2A and 2B are schematic representations of a system in accordance with the present disclosure in which each of the outlet lines from the separator has a flow control device in the form of a clamp with the first outlet line or retentate line open/second outlet line or filtrate line closed (FIG. 2A) and the retentate line closed/filtrate line open (FIG. 2B).
Figure 2B:
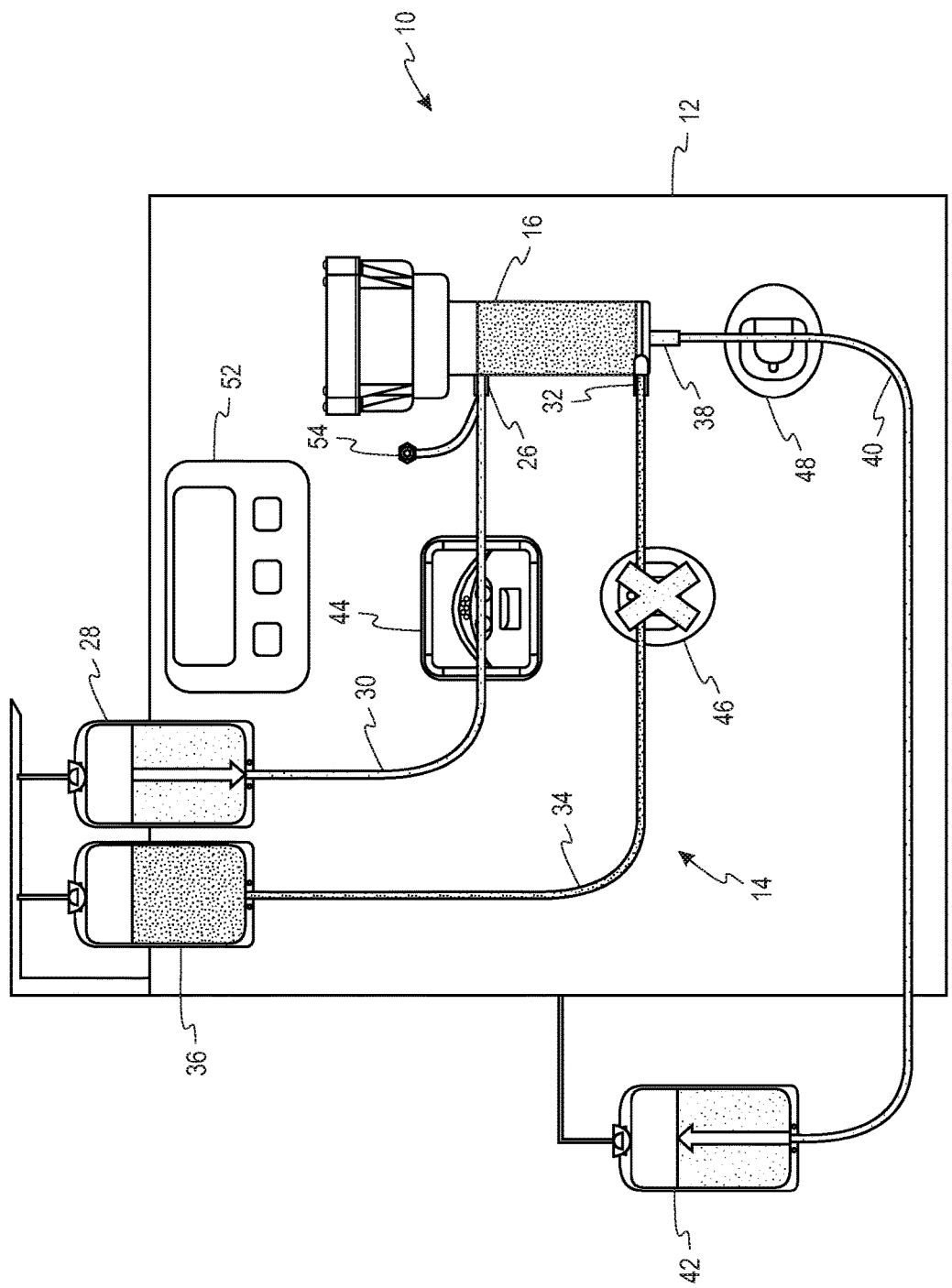
Figure 3A:
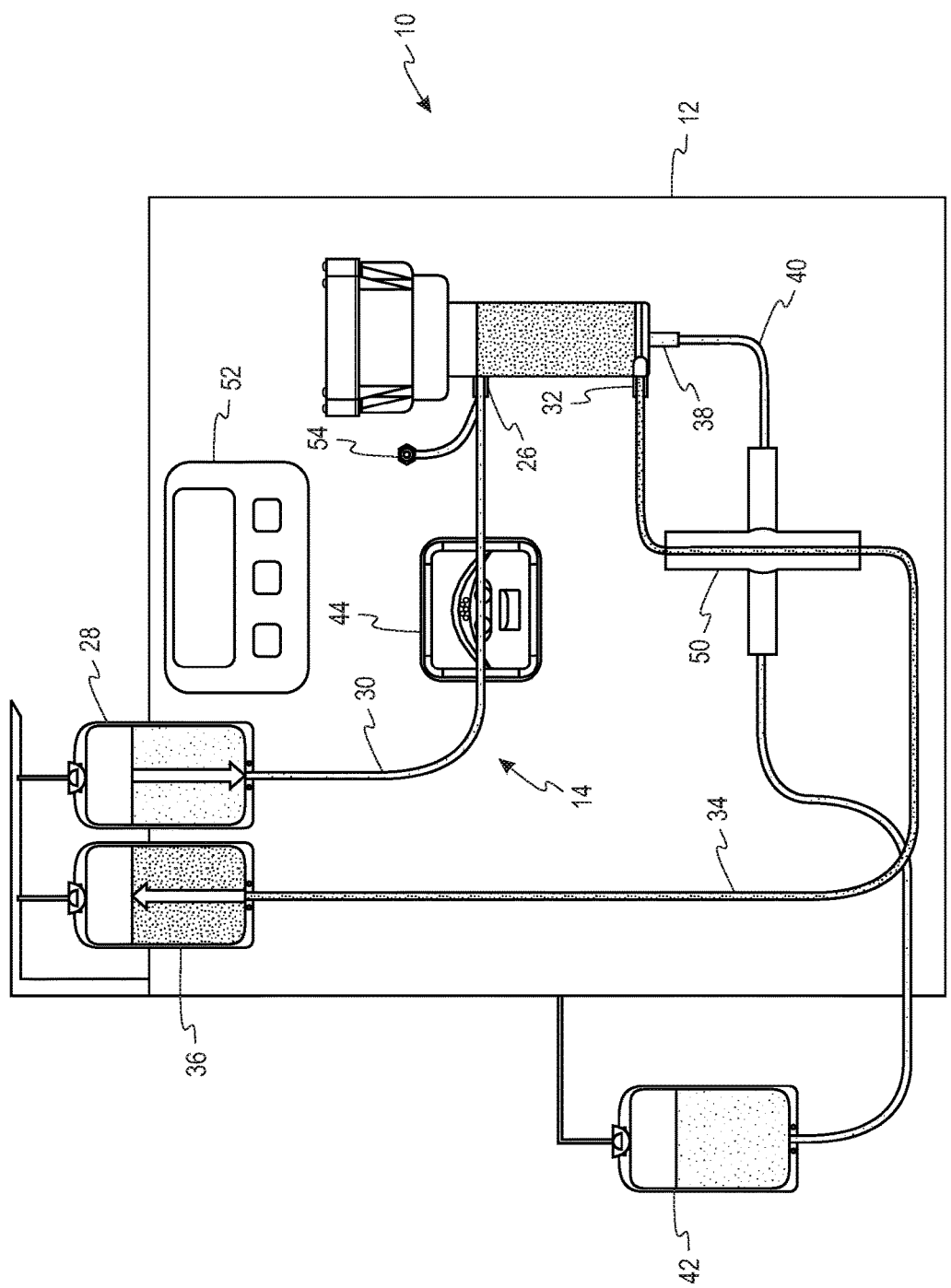
FIGS. 3A and 3B are schematic representations of a system in accordance with the present disclosure in which both of the outlet lines from the separator share a common flow control device in the form of a two-position stopcock with the retentate line open/filtrate line closed (FIG. 3A) and the retentate line closed/filtrate line open (FIG. 3B).
Figure 3B:
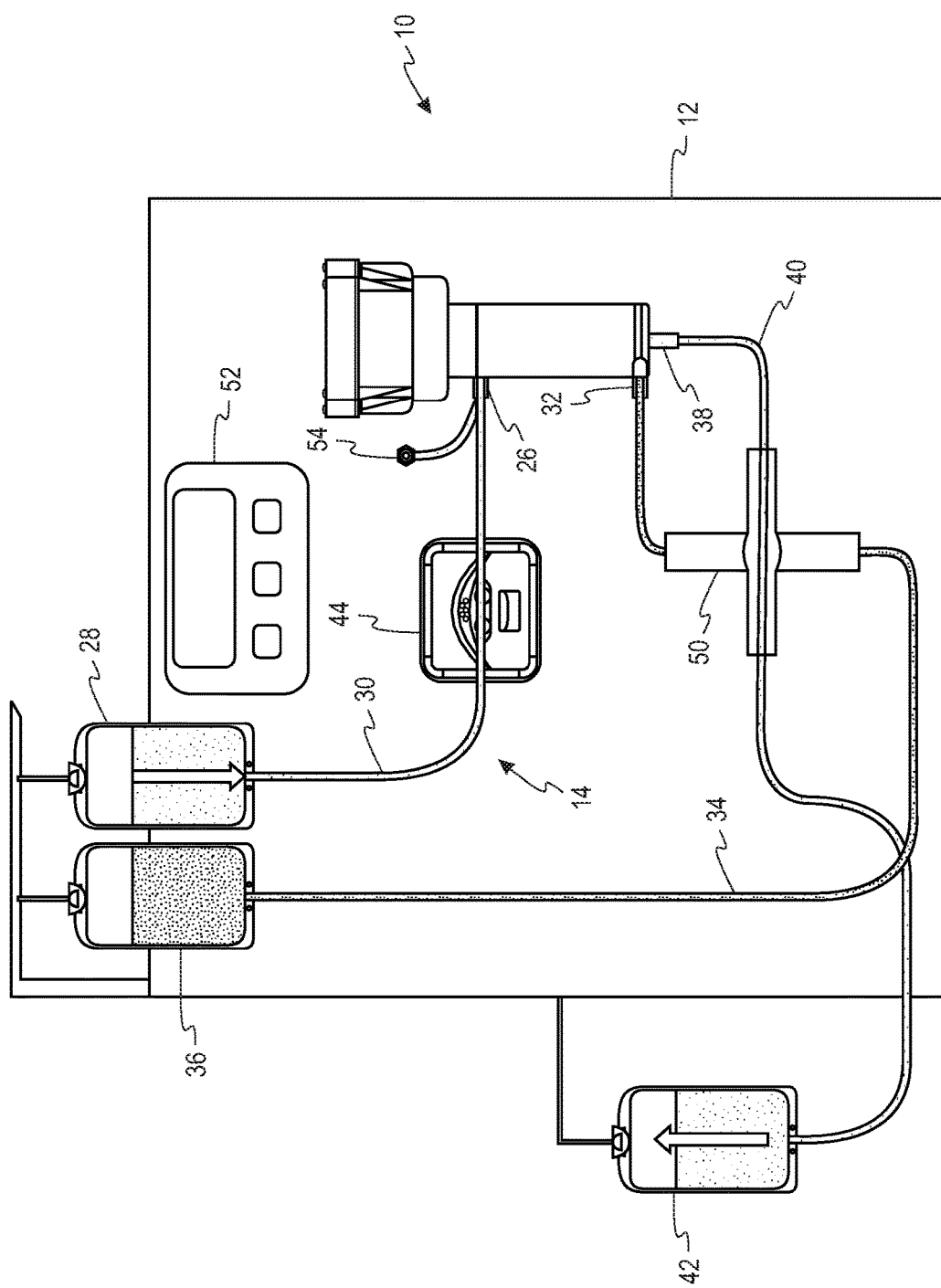

Specifically, the flow rate of retentate and filtrate out of the separator is controlled by alternating or pulsing between an open and closed retentate line 34, with the filtrate line 40 being open or closed in opposition to the retentate line 34 (i.e., if retentate line 34 is closed, filtrate line 40 must be open, and vice versa). The alternating of the open and closed states for the retentate and filtrate lines is illustrated in FIGS. 2A and 2B, in which each of the retentate and filtrate lines 34, 40 has a clamp 46, 48 associated therewith (with an "X" through the clamp indicating that the clamp has closed its associated tubing segment), and in FIGS. 3A and 3B, in which the retentate and filtrate lines 34, 40 share a common two-position stopcock 50. Modulation of the "retentate line open" pulse width (i.e., changing how long the retentate line is open vs. closed) allows for the retentate rate (and filtrate rate) to be changed and controlled. Alternating the flow control devices between open and closed states, with a specific duty cycle, will lead to an "average" output flow rate somewhere in between the flow rates obtained in the open and closed states.

Figure 4:
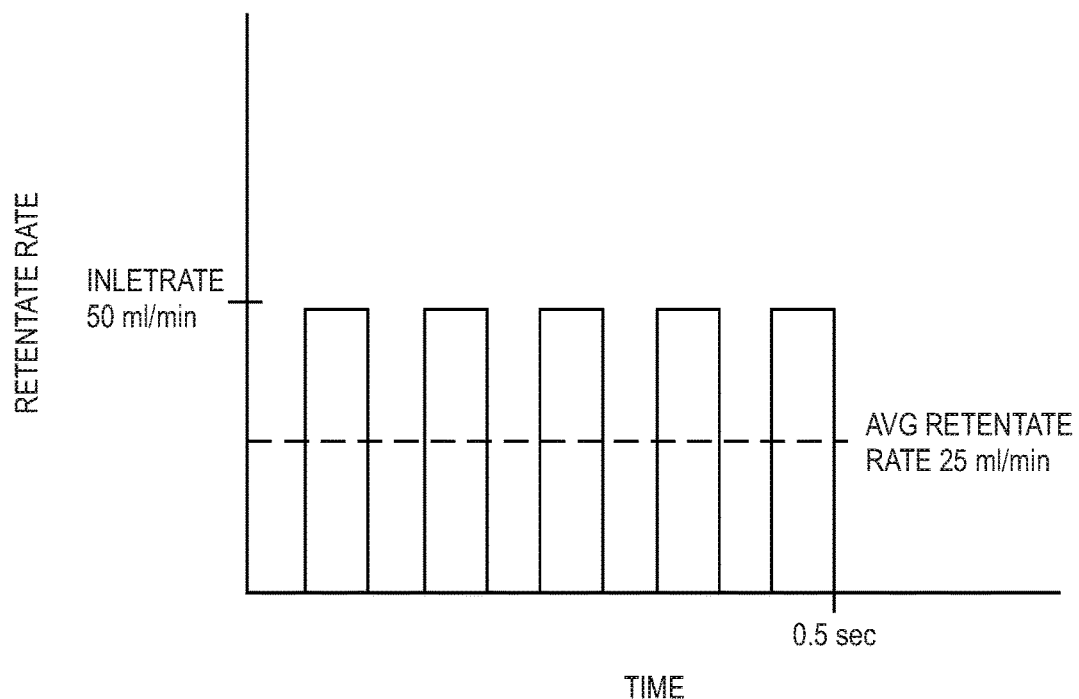
FIGS. 4-6 are plots of retentate rate vs. time for duty cycles of 50%, 10% and 80%, respectively, showing the average retentate flow rate under such conditions.

For example, and presuming that the retentate and filtrate clamps 46 and 48 are in opposing states, if the inlet pump is flowing at 50 ml/min and the retentate line is closed, the flow through the retentate line is the equal to 0 ml/min, but if the retentate line is open, flow through the line is 50 ml/min. This scenario is depicted in FIG. 4, in which the retentate line opens and closes with a duty cycle of 50% to produce an average retentate flow rate of 25 ml/min. If the retentate line alternates between open and closed states is sufficiently fast relative to the mechanical compliance of the tubing kit, the average output rate will be substantially constant over time.

The duty cycle, or percentage of time the retentate line is open, required to achieve a targeted retentate flow rate is equal to the ratio of the target retentate rate to the constant inlet pump rate.

$$\text{Duty Cycle} = \frac{\text{Target Retentate Rate}}{\text{Inlet Rate}}$$

To determine the amount of time which the retentate line should be open/closed over a specific time period to achieve the targeted rate, the Duty Cycle calculated above can be divided by the desired frequency (how often the flow control devices are to be opened and closed) according to the definition of a duty cycle:

$$\text{Duty Cycle} = \frac{\text{Time Active}}{\text{Signal Time Period}} = \frac{\text{Time Retentate Line Open}}{\text{Signal Time Period}}$$

$$\text{Where: Signal Time Period} = \frac{1}{\text{Frequency}}$$

$$\text{Time Retentate Line Open} = \frac{\text{Duty Cycle}}{\text{Frequency}}$$

$$\text{Time Retentate Line Closed} = \text{Signal Time Period} - \text{Time Retentate Line Open}$$

The duty cycle is dependent only on the desired retentate flow rate for a given inlet rate. Thus, the retentate flow rate has the potential to be any value in practice, and will vary depending on target retentate rates unique to each application. Inlet rates are also dependent on the application.

Retentate rates are selected to achieve a targeted outlet concentration based on a known inlet concentration of cells according to the following relationship: Retentate Rate= (Inlet Rate×Inlet Cell Concentration [HCT])/Target Outlet Cell Concentration [HCT]. For example, in whole blood filtration in which the inlet flow rate is 50 ml/min and the blood is 40% HCT, if a target of 80% retentate HCT is desired, the retentate rate is equal to (50×40)/80=25 ml/min.

Applications such as cell washing or platelet rich plasma volume reduction will tend to have lower duty cycles, as the retentate flow rates are typically very low compared to inlet flow rates. Applications such as whole blood filtration or plasmapheresis would apply higher duty cycles, as the retentate rate is around half of the inlet rate. For example, platelet rich plasma volume reduction application may apply an inlet flow rate around 25 ml/min and target a retentate rate of 5 ml/min, leading to a duty cycle of 20%. On the other hand, whole blood filtration may apply an inlet flow rate of 50 ml/min, and target a retentate rate around 25 ml/min, leading to a duty cycle of 50%. Duty cycles of as high as 80-90%, may be applied during priming applications, or during procedures as well.

The duty cycle is selected regardless of how it affects the transmembrane pressure (TMP) of the spinning membrane separator. However, a particular duty cycle can have an impact on the measured TMP if the correct frequency is not chosen. For example, a duty cycle of 50% at a frequency of 1 Hz may cause the measured TMP to oscillate, since the retentate line is open/closed relatively slowly, whereas a duty cycle of 50% with an outlet line open/close frequency of 10 Hz may pulse fast enough for the measured TMP to be smooth over time. Thus, a sufficiently high frequency is selected that, regardless of the duty cycle, the flow is no more pulsatile, and potentially less pulsatile, than when the flow is controlled by a pump associated with one of the outlet lines. This, in turn, will cause the measured TMP to be no more pulsatile than that experienced when a pump is used to control the output flow rate.

The preferred frequency will likely vary depending on application. In general, applications involving red blood cells (like whole blood filtration or plasmapheresis) will likely utilize higher frequencies than applications involving only platelets or white blood cells (like cell washing), as the overall cell volume of whole blood filtration procedures is significantly higher than that of cell washing procedures, which would result in membrane fouling and hemolysis if outlet line is not pulsed at a sufficiently high frequency.

EXAMPLES FOLLOW

Figure 5:
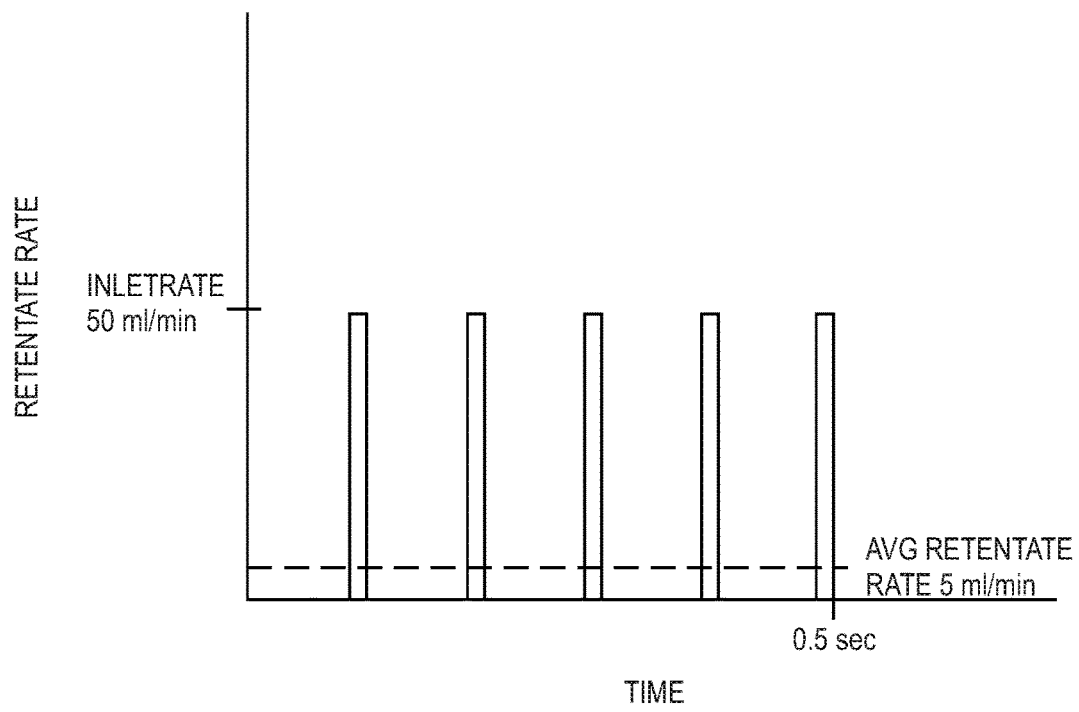

Example 1 (FIG. 5): Inlet Rate=50 Ml/Min, Target Retentate Rate=5 Ml/Min, Frequency 10 Hz $$\text{Duty Cycle} = \frac{\text{Target Retentate Rate}}{\text{Inlet Rate}} = \frac{5}{50} = 0.1$$

-continued $$\text{Signal Time Period} = \frac{1}{\text{Frequency}} = \frac{1}{10 \text{ Hz}} = 0.1 \text{ sec}$$

$$\text{Time Retentate Line Open} = \frac{\text{Duty Cycle}}{\text{Frequency}} = \frac{0.1}{10} = 0.01 \text{ sec}$$

Time Retentate Line Closed =

Signal Time Period − Time Retentate Line Open =

$$0.1 \text{ sec} - 0.01 \text{ sec} = 0.09 \text{ sec}$$

Figure 6:
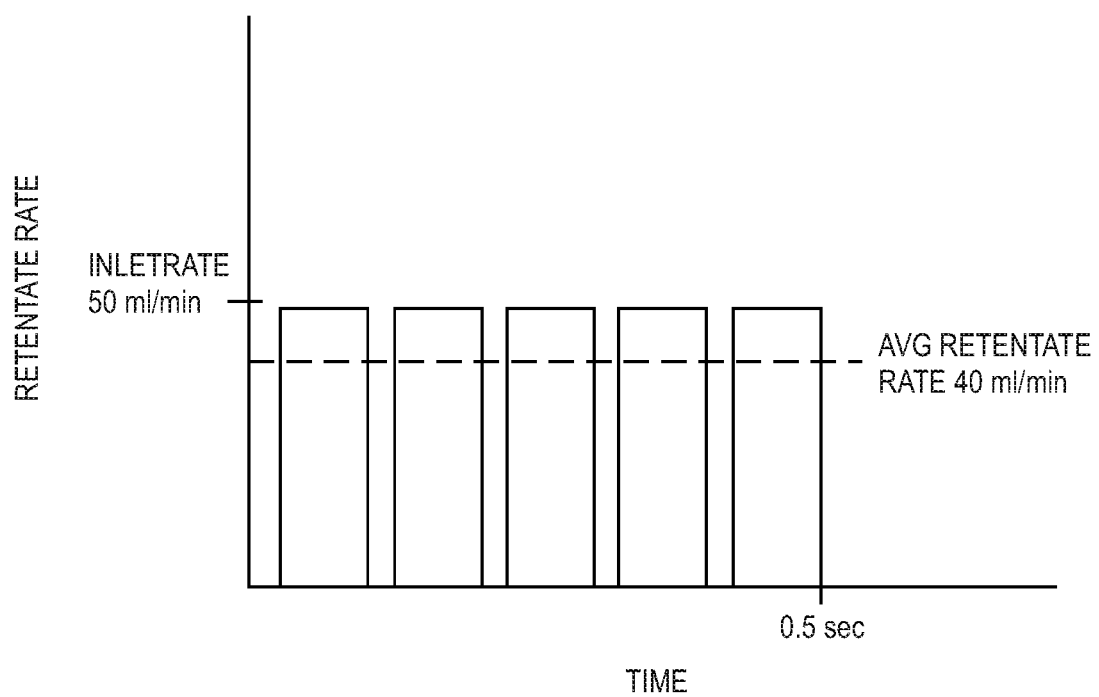

Example 2 (FIG. 6): Inlet rate=50 Ml/Min, Target Retentate Rate=40 Ml/Min, Frequency 10 Hz $$\text{Duty Cycle} = \frac{\text{Target Retentate Rate}}{\text{Inlet Rate}} = \frac{40}{50} = 0.8$$

$$\text{Signal Time Period} = \frac{1}{\text{Frequency}} = \frac{1}{10 \text{ Hz}} = 0.1 \text{ sec}$$

$$\text{Time Retentate Line Open} = \frac{\text{Duty Cycle}}{\text{Frequency}} = \frac{0.8}{10} = 0.08 \text{ sec}$$

Time Retentate Line Closed =

Signal Time Period − Time Retentate Line Open =

$$0.1 \text{ sec} - 0.08 \text{ sec} = 0.02 \text{ sec}$$

Thus, an improved spinning membrane separation system and method have been provided in which the number of components has been reduced over prior systems, thus facilitating simplification of the design and reduction is size for the system. The system and method should also provide for greater accuracy in controlling the outlet flow from the separator, as discrepancies between the target flow rate and actual flow rate through peristaltic pumps due to, e.g., pump inlet and outlet pressures, tubing dimensions and tolerances, and pump motor rotation errors, will no longer affect the outlet flow from the separator.

We claim:

1. A system for separating a suspension of biological cells comprising:
    a) a fluid circuit comprising a spinning membrane separator having a housing and a filter membrane having a first side and a second side, a gap being defined between the housing and the first side of the filter membrane and a flow path in fluid communication with the second side of the filter membrane, an inlet for introducing the suspension of biological cells into the gap, a first outlet in communication with the gap for flowing the first type of cells from the separator and a second outlet in communication with the second side of the filter membrane for flowing the second type of cells from the separator;
    b) a hardware component comprising a pump for flowing the suspension of biological cells to the inlet of the separator, at least one flow control device associated with the first outlet and the second outlet of the separator for selectively opening and closing the first and second outlets so as to permit either the first type of cells or the second type of cells to flow out of the separator, and a programmable controller configured to operate the pump so as to flow the suspension of biological cells to the inlet of the separator at a predetermined inlet flow rate and to alternately open and close the flow control device in accordance with a predetermined duty cycle.

2. The system of claim 1 wherein the programmable controller is configured to alternately open and close the flow control device such that the duty cycle is equal to the ratio of a target flow rate of first type of cells through the first outlet to the predetermined inlet flow rate.

3. The system of claim 2 wherein the programmable controller is further configured to determine the target flow rate of the first type of cells as the product of the inlet flow rate times the ratio of cell concentration of the suspension of biological cells to a target cell concentration of the first type of cells.

4. The system of claim 1 wherein the programmable controller is further configured to alternately open and close the flow control device at a predetermined frequency.

5. The system of claim 4 wherein the programmable controller is further configured to establish the predetermined frequency for the duty cycle based on the concentration of cells in the suspension of biological cells being separated.

6. The system of claim 5 wherein the predetermined frequency for the duty cycle is directly proportional to the concentration of cells in the suspension of biological cells being separated.

7. The system of claim 1 wherein the flow control device is a clamp associated with each of the first and second outlets of the separator.

8. The system of claim 1 wherein the flow control device is a two position stopcock associated with both of the first and second outlets of the separator.

9. A system for separating a suspension of biological cells comprising:
    a) a fluid circuit comprising either a spinning membrane separator or a centrifugal separator, the separator having a housing with an inlet for introducing the suspension of biological cells into the separator, a first outlet for flowing a first type of cells from the separator and a second outlet for flowing a second type of cells from the separator;
    b) a hardware component comprising a pump for flowing the suspension of biological cells to the inlet of the separator, at least one flow control device associated with the first outlet and the second outlet of the separator for selectively opening and closing the first and second outlets so as to permit either the first type of cells or the second type of cells to flow out of the separator, and a programmable controller programmed to operate the pump so as to flow the suspension of biological cells to the inlet of the separator at a predetermined inlet flow rate and to alternately open and close the flow control device in accordance with a predetermined duty cycle.

10. The system of claim 9 wherein the programmable controller s configured to alternately open and close the flow control device such that the duty cycle is equal to the ratio of a target flow rate of first type of cells through the first outlet to the predetermined inlet flow rate.

11. The system of claim 10 wherein the programmable controller is further configured to determine the target flow rate of the first type of cells as the product of the inlet flow rate times the ratio of cell concentration of the suspension of biological cells to a target cell concentration of the first type of cells.

12. The system of claim 9 wherein the programmable controller is further configured to alternately open and close the flow control device at a predetermined frequency.

13. The system of claim 12 wherein the programmable controller is further configured to establish the predetermined frequency for the duty cycle based on the concentration of cells in the suspension of biological cells being separated.

14. The system of claim 13 wherein the predetermined frequency for the duty cycle is directly proportional to the concentration of cells in the suspension of biological cells being separated.

15. The system of claim 9 wherein the flow control device is a clamp associated with each of the first and second outlets of the separator.

16. The system of claim 9 wherein the flow control device is a two position stopcock associated with both of the first and second outlets of the separator.

\* \* \* \* \*